United States Patent [19]

Gabrielsen et al.

[11] Patent Number: 4,507,479
[45] Date of Patent: Mar. 26, 1985

[54] COLOR-FORMING SULFONAMIDODIPHENYLAMINE DYE PRECURSOR THAT PRODUCES PHENAZINE DYE

[75] Inventors: Rolf S. Gabrielsen, Webster; Patricia A. Graham, Williamson; James E. Klijanowicz, Pittsford, all of N.Y.

[73] Assignee: Eastman Kodak Company, Rochester, N.Y.

[21] Appl. No.: 426,576

[22] Filed: Sep. 29, 1982

Related U.S. Application Data

[62] Division of Ser. No. 280,628, Jul. 6, 1981, Pat. No. 4,380,666.

[51] Int. Cl.³ .............................. C07D 241/46
[52] U.S. Cl. ....................................... 544/348
[58] Field of Search ........................................ 544/348

[56] References Cited

U.S. PATENT DOCUMENTS

| | | | |
|---|---|---|---|
| 3,482,971 | 12/1969 | Bloom et al. | 430/242 |
| 3,498,785 | 3/1970 | Bloom et al. | 430/223 |
| 3,622,603 | 11/1971 | Bloom et al. | 260/397.7 R |
| 3,658,524 | 4/1972 | Piesach | 430/223 |
| 3,821,200 | 6/1974 | Stingl | 260/239.7 |
| 3,938,995 | 2/1976 | Gompf et al. | 430/367 |
| 4,110,355 | 8/1978 | Bloom | 260/372 |

OTHER PUBLICATIONS

Hideo et al., Chem. Abstracts, vol. 66, (1967): 36499w.
Riesz et al., Chem. Abstracts, vol. 69, (1968): 20395k.

Primary Examiner—Donald G. Daus
Assistant Examiner—William A. Teoli, Jr.
Attorney, Agent, or Firm—Richard E. Knapp

[57] ABSTRACT

A color-forming sulfonamidodiphenylamine dye precursor has sulfonamido groups in the ortho position and para position in relation to the —NH— moiety of the sulfonamidodiphenylamine and, in oxidized form, intramolecularly reacts to produce a sulfonamido-substituted phenazine dye. Such color-forming sulfonamidodiphenylamine dye precursors are useful to produce a dye image by cross-oxidation in an imaging material.

7 Claims, No Drawings

COLOR-FORMING SULFONAMIDODIPHENYLAMINE DYE PRECURSOR THAT PRODUCES PHENAZINE DYE

This is a division of application Ser. No. 280,628 filed July 6, 1981, now U.S. Pat. No. 4,380,666.

FIELD OF THE INVENTION

This invention relates to a color-forming sulfonamidodiphenylamine dye precursor that (i) has sulfonamido groups in the ortho postion and para position in relation to the —NH— moiety of the sulfonamidodiphenylamine, and (ii), in oxidized form, intramolecularly reacts to produce a sulfonamido-substituted phenazine dye. An aspect of the invention relates to phenazine dyes formed from such sulfonamidodiphenylamines. Another aspect relates to a method of preparing the color-forming sulfonamidodiphenylamines.

DESCRIPTION OF THE STATE OF THE ART

Photographic materials for producing silver and dye images are well known. It has been desirable to provide alternative means for producing a dye image, especially a dye image that enhances a silver image, other than by coupling reactions. Coupling reactions for forming dye images are described in, for example, U.S. Pat. No. 3,938,995. The present invention provides compounds that avoid the need for a coupling reaction to produce a dye, especially a phenazine dye, that is suitable as an image in a photographic material.

Reducing agents are known that autoreact intramolecularly to form a heterocyclic ring. Such reducing agents are described in, for example, U.S. Pat. No. 3,482,971 and U.S. Pat. No. 3,622,603. The reducing agents in these patents are formed by means of a hydroxy (OH) group or amino group in the position para to an —NH— group in the compounds. The compounds of the present invention have no such hydroxy group or amino group. The compounds of U.S. Pat. No. 3,482,971 and U.S. Pat. No. 3,622,603 are not disclosed as color-providing materials, but rather as reducing agents and scavengers for oxidized reducing agents.

SUMMARY OF THE INVENTION

It has been found according to the invention that a color-forming sulfonamidodiphenylamine dye precursor having sulfonamido groups in the ortho position and para position in relation to the —NH— moiety of the sulfonamidodiphenylamine is capable, in oxidized form, of intramolecular reaction to produce a sulfonamido-substituted phenazine dye. These color-forming sulfonamidodiphenylamine dye precursors are useful to form corresponding phenazine dyes, preferably in photographic materials.

The color-forming sulfonamidodiphenylamine dye precursor is especially useful in an imaging material, such as a photographic silver halide material, to form a phenazine dye image by a cross-oxidation reaction. The color-forming sulfonamidodiphenylamine dye precursor does not have reducing properties that adversely affect image formation. In addition, the corresponding phenazine dye is useful as an image dye alone or as an image dye that enhances a metal image, such as a silver image, in an imaging material. The phenazine dye is also useful as a colorant for textiles, varnishes, waxes, leather, plastics, paper and paints.

DETAILED DESCRIPTION OF THE INVENTION

Many color-forming sulfonamidodiphenylamines are dye precursors according to the invention and are useful in imaging materials. Combinations of color-forming sulfonamidodiphenylamine dye precursors are also useful, if desired. Examples of color-forming sulfonamidodiphenylamine dye precursors according to the invention are represented by the formula:

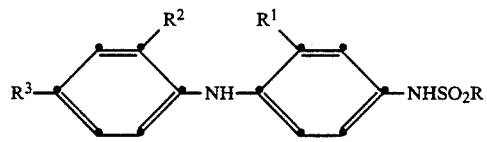

wherein:
R is alkyl containing 1 to 20 carbon atoms, such as methyl, ethyl, propyl, butyl, decyl and eicosyl, aryl containing 6 to 20 carbon atoms, such as phenyl, para-tolyl and 2,4,6-triisopropylphenyl, or alkaryl containing 7 to 20 carbon atoms, such as benzyl;

$R^1$ and $R^2$ are individually hydrogen, alkyl containing 1 to 4 carbon atoms, such as methyl, ethyl, propyl or butyl, or —NHSO$_2$R$^4$; and at least one of $R^1$ and $R^2$ is —NHSO$_2$R$^4$;

$R^3$ is alkoxy containing 1 to 20 carbon atoms, such as methoxy, ethoxy, propoxy, and butoxy, alkyl containing 1 to 20 carbon atoms, such as methyl, ethyl, propyl, decyl and eicosyl, or

$R^4$ is alkyl containing 1 to 20 carbon atoms, such as methyl, ethyl, propyl, decyl and eicosyl, aryl containing 6 to 20 carbon atoms, such as phenyl, para-tolyl and 2,4,6-triisopropylphenyl or alkaryl containing 7 to 20 carbon atoms, such as benzyl and xylyl;

$R^5$ is hydrogen or alkyl containing 1 to 20 carbon atoms, such as methyl, ethyl, propyl, decyl and eicosyl; and $R^6$ is alkyl containing 1 to 20 carbon atoms, such as methyl, ethyl, propyl, butyl, decyl and eicosyl.

The terms "alkyl" and "aryl" herein include unsubstituted alkyl, such as unsubstituted methyl, ethyl, propyl and butyl, and unsubstituted aryl, such as unsubstituted phenyl. The terms also include alkyl and aryl that are substituted by groups which do not adversely affect the desired properties of the sulfonamidodiphenylamines according to the invention or the corresponding phenazine dyes. Examples of useful substituted alkyl groups include alkyl substituted by alkoxy, hydroxyalkoxy, carboxamido or methylsulfonamido groups. Examples of substituted aryl include methoxyphenyl, 2,4,6-triisopropylphenyl and tolyl.

An optimum color-forming sulfonamidodiphenylamine dye precursor according to the invention will depend upon such factors as the intended use, such as the desired image and an imaging material, processing steps and conditions in forming an image in the imaging material, particular photosensitive silver halide and the imaging material containing the sulfonamidodiphenylamine dye precursor, and other components in the imaging material.

An especially useful color-forming sulfonamidodiphenylamine dye precursor according to the invention is one wherein R in the noted formula is 2,4,6-triisopropylphenyl:

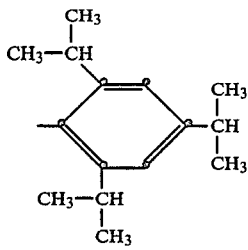

This group helps provide increased light stability to the resulting phenazine dye upon processing of the color-forming sulfonamidodiphenylamine dye precursor in a photographic silver halide material.

Examples of useful color-forming sulfonamidodiphenylamine dye precursors include:

2,4-Bis methylsulfonamido-4'-diethylaminodiphenylamine represented by the formula:

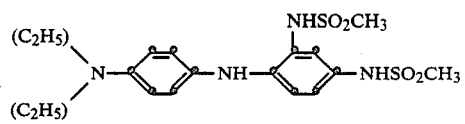

2'-Methylsulfonamido-4'-(2,4,6-triisopropylphenyl)-sulfonamido 2-methyl-4-(2-methanesulfonamido)ethylethylamino diphenylamine represented by the formula:

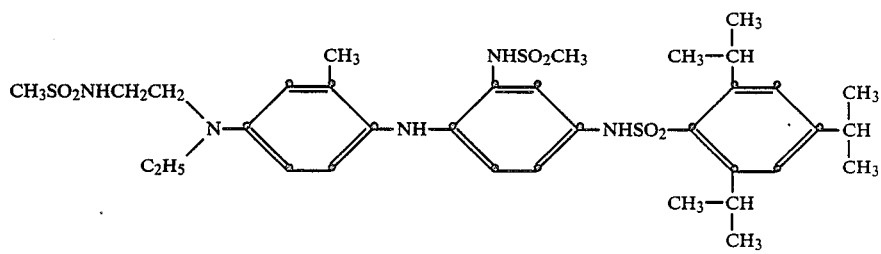

A 2,4,6-triisopropylphenyl group is also designated herein as follows:

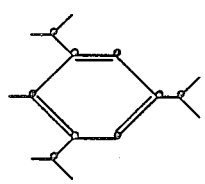

2'-Methylsulfonamido-4'-(2,4,6-triisopropyl)benzenesulfonamido-4-trisethyloxyethanol diphenylamine represented by the formula:

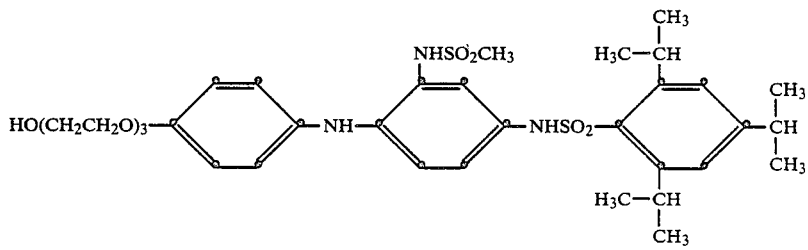

4-($\beta$-Methanesulfonamidoethyl)ethylamino-2-methyl-2',4'-bis(2,4,6-triisopropyl)phenylsulfonamido diphenylamine represented by the formula:

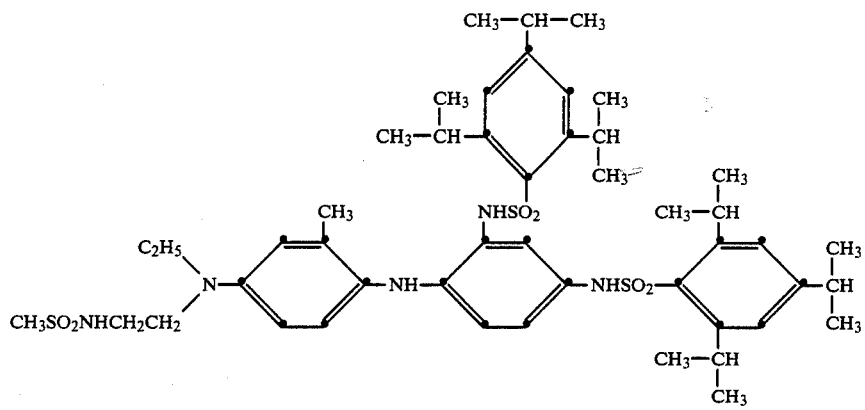

2,4'-Bismethylsulfonamido-4-N,N-diethylamino diphenylamine represented by the formula:

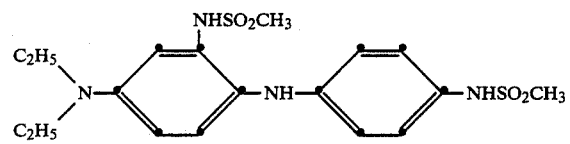

4-n-Hexyloxy-2'-methanesulfonamido-4'-(2,4,6-triisopropylphenyl)sulfonamido diphenylamine represented by the formula:

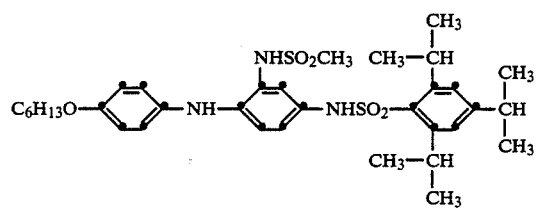

4-Methoxy-2'-methanesulfonamido-4'-(2,4,6-tri-isopropyl)phenylsulfonamido diphenylamine represented by the formula:

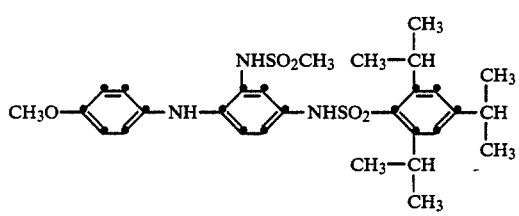

Each of the color-forming sulfonamidodiphenylamine dye precursors according to the invention forms a corresponding phenazine dye by intramolecular reaction.

A method of preparing a color-forming sulfonamidodiphenylamine according to the invention comprises the steps:

I reacting (A) represented by the formula:

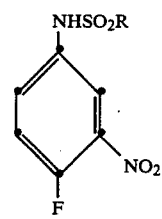

with
B represented by the formula:

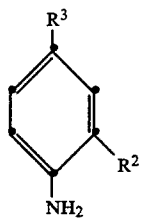

wherein R, $R^2$ and $R^3$ are as defined, to produce a nitro-substituted sulfonamidodiphenylamine;

II reducing the resulting nitro substituted sulfonamidodiphenylamine from (I) by means of hydrogen in the presence of a suitable catalyst, preferably a Raney nickel catalyst; and, purifying the resulting intermediate amine substituted sulfonamidodiphenylamine; then, III dissolving the purified amine substituted sulfonamidodiphenylamine from (II) in a suitable organic solvent, such as pyridine, and reacting the amine substituted sulfonamidodiphenylamine with a suitable sulfonyl chloride to form the color-forming sulfonamidodiphenylamine according to the invention.

An example of such a process of preparing a color-forming sulfonamidodiphenylamine dye precursor according to the invention is the preparation of 2,4-bis methylsulfonamido-4'-diethylaminodiphenyl-amine represented by the formula:

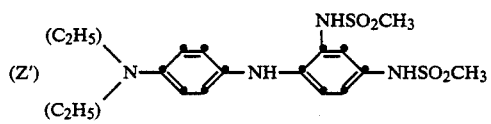

The process of preparing this color-forming sulfonamidodiphenylamine dye precursor comprises the steps:

I reacting a fluorine substituted compound represented by the formula:

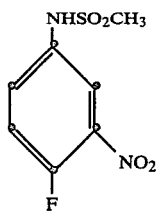

with an amine represented by the formula:

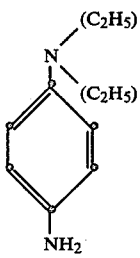

to release hydrogen fluoride (HF) and to form:

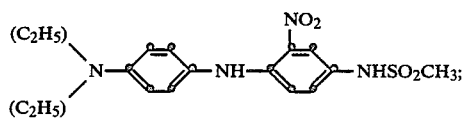

then,

II reducing the resulting nitro substituted sulfonamidodiphenylamine from (I) by means of hydrogen in the presence of suitable catalyst, such as a Raney nickel catalyst; and, purifying the resulting intermediate amine substituted sulfonamidodiphenylamine; then, III dissolving the purified, amine substituted sulfonamidodiphenylamine from (II) in a suitable solvent, such as pyridine, and reacting the amine substituted sulfonamidodiphenylamine with methanesulfionyl chloride to form the desired sulfonamidodiphenylamine according to the invention.

The described preparation of a color-forming sulfonamidodiphenylamine according to the invention is generally carried out at atmospheric pressure. Step (I) in the process is generally carried out in the presence of a suitable solvent, such as alpha-picoline, 2,6-lutedine, pyridine, beta-picoline and gamma-picoline. This step involving the production of the nitro substituted intermediate is generally carried out at reflux temperature under a nitrogen atmosphere to prevent adverse interference from oxygen or other components in the atmosphere. The nitro substituted sulfonamidodiphenylamine intermediate is generally separated and purified prior to a reduction in step (II) of the process. This separation and purification is carried out by conventional techniques in the organic synthesis art, such as recrystallization processes.

The reduction in step (II) of the process according to the invention involves use of hydrogen in the presence of a suitable catalyst. This catalyst is preferably a Raney nickel catalyst. Other useful catalysts are palladium on carbon and platinum on carbon. The conditions under which the reduction is carried out in step (II) will depend upon such factors as the particular intermediate, the presence of a solvent, the particular catalyst, and the desired intermediate amine substituted sulfonamidodiphenylamine.

In step (III) of a process of the invention, a sulfonyl chloride is suitable which provides a sulfonamido group in the ortho position in relation to the —NH— group of the color-forming sulfonamidodiphenylamine dye precursor according to the invention. Many sulfonyl chlorides are useful. Examples of suitable sulfonyl chlorides include alkylsulfonyl chlorides, arylsulfonyl chlorides and alkaryl sulfonyl chlorides containing up to 20 carbon atoms. The alkyl, aryl or alkaryl group of the sulfonyl chloride corresponds to the alkyl, aryl or alkaryl group for $R^1$ as defined for the color-forming sulfonamidodiphenylamine dye precursor. Examples of useful sulfonyl chlorides include methanesulfonyl chloride, triisopropylphenyl sulfonyl chloride, butanesulfonyl chloride and paratoluenesulfonyl chloride.

A solvent is suitable in step (III) of the process of the invention which is compatible with the intermediate purified amine substituted sulfonamidodiphenylamine from step (II). Pyridine is an especially useful solvent. Examples of other useful solvents include: alpha-picoline and dioxane with triethylamine. Selection of an optimum solvent will depend upon such factors as the particular intermediate amine substituted sulfonamidodiphenylamine, the particular sulfonyl chloride, reaction conditions and the desired color-forming sulfonamidodiphenylamine dye precursor.

Many phenazine dyes are prepared from the color-forming sulfonamidodiphenylamine dye precursors according to the invention. Combinations of phenazine dyes are prepared, if desired. Examples of useful phenazine dyes prepared from the color-forming sulfonamidodiphenylamine dye precursors include those represented by the formula:

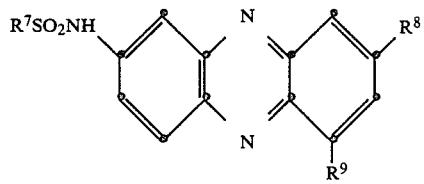

wherein:

$R^7$ is alkyl containing 1 to 20 carbon atoms, such as methyl, ethyl, propyl, butyl, decyl and eicosyl, aryl containing 6 to 20 carbon atoms, such as phenyl, para-tolyl and 2,4,6-triisopropylphenyl, or alkaryl containing 7 to 20 carbon atoms, such as benzyl and xylyl;

$R^8$ is alkoxy containing 1 to 20 carbon atoms, such as methoxy, ethoxy, propoxy and butoxy, alkyl containing 1 to 20 carbon atoms, such as methyl, ethyl, propyl, decyl and eicosyl, or

$R^9$ is hydrogen, alkyl containing 1 to 4 carbon atoms, such as methyl, ethyl, propyl and butyl, or —NH-SO$_2$R$^{12}$;

$R^{10}$ is hydrogen or alkyl containing 1 to 20 carbon atoms, such as methyl, ethyl, propyl, butyl, decyl and eicosyl;

$R^{11}$ is alkyl containing 1 to 20 carbon atoms, such as methyl, ethyl, propyl, butyl, decyl and eicosyl; and, $R^{12}$ is alkyl containing 1 to 20 carbon atoms, such as methyl, ethyl, propyl, butyl, decyl and eicosyl, aryl containing 6 to 20 carbon atoms, such as phenyl, paratolyl and 2,4,6-triisopropyl, or alkaryl containing 7 to 20 carbon atoms, such as benzyl and xylyl.

An especially useful phenazine dye is one wherein R is 2,4,6-triisopropylphenyl. This group provides increased stability for the phenazine dye in, for example, an imaging material.

Selection of an optimum phenazine dye according to the invention will depend upon such factors as the desired end use, such as the particular imaging material in which the phenazine dye is to be used, other components in the imaging material, and the desired color of the dye. Examples of useful phenazine dyes according to the invention include:

2-Diethylamino-7-methanesulfonamido phenazine represented by the formula:

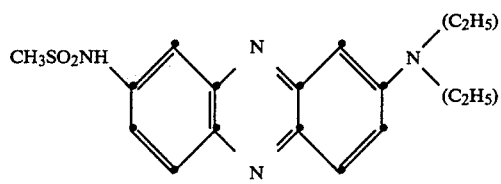

2-N-Ethyl-N-(β-methanesulfonamido)ethylamino-4-methyl-7-(2,4,6-triisopropyl)phenylsulfonamido phenazine represented by the formula:

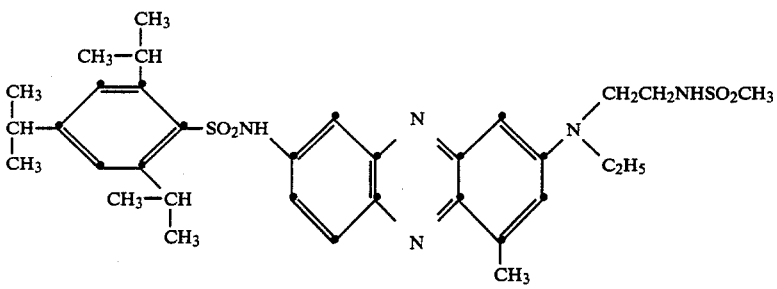

2-Trisethyloxyethanol-7-(2,4,6-triisopropyl)phenyl-sulfonamido phenazine represented by the formula:

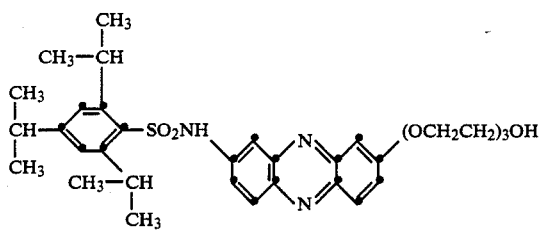

2-n-Hexyloxy-7-(2,4,6-triisopropyl)phenylsulfonamido phenazine represented by the formula:

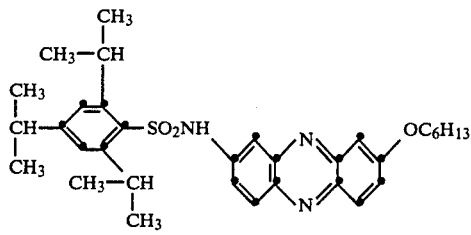

2-Methoxy-7-(2,4,6-triisopropyl)benzenesulfonamidophenol represented by the formula:

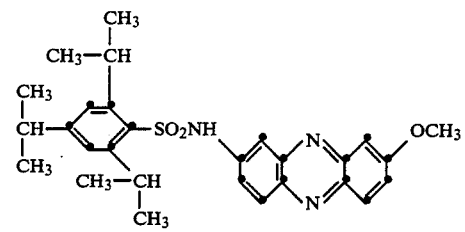

The hue of the phenazine dye according to the invention will vary, depending upon such factors as the particular groups on the color-forming sulfonamidodiphenylamine dye precursor, processing conditions for preparation of the phenazine dye, other components in the composition containing the phenazine dye, such as dispersion solvents, and the physical form of the dye. In an imaging material, such as a photographic silver halide material, the color-forming sulfonamidodiphenylamine dye precursor is generally colorless or slightly colored prior to processing. Some of the starting color-forming sulfonamidodiphenylamine dye precursors have a slight yellow color in an imaging material. This slight color is not considered unacceptable in many imaging materials.

The term "color-forming" herein means that the sulfonamidodiphenylamine dye precursor in an imaging material does not absorb radiation to an undesired degree in the visible region of the electromagnetic spectrum. In some imaging materials, such as in some photographic silver halide materials, the sulfonamidodiphenylamine dye precursor absorbs radiation in certain areas of the electromagnetic spectrum which does not adversely affect the desired properties or the desired image of the phenazine dye formed upon processing.

A process of preparing a phenazine dye according to the invention comprises (I) oxidizing a color-forming sulfonamidodiphenylamine according to the invention by means of an oxidizing agent, preferably the oxidized form of a 3-pyrazolidone reducing agent. This preparation and reaction is preferably carried out in an imaging material, such as a photographic silver halide material, in which the phenazine dye is formed imagewise.

In photographic silver halide materials, many cross-oxidizing reducing agents, also described as cross-oxidizing developing agents (COD), are useful for producing a phenazine dye according to the invention. Any silver halide developing composition is useful according to the invention for cross-oxidizing purposes, provided it comprises a major proportion of a cross-oxidizing reducing agent, which will cross-oxidize the sulfonamidodiphenylamine precursor to the desired phenazine dye. Such a cross-oxidizing reducing agent becomes oxidized during development of a silver halide photographic material by reducing exposed silver halide to silver metal. The oxidized reducing agent then cross-oxidizes the sulfonamidodiphenylamine dye precursor.

In a photographic silver halide material, a cross-oxidizing reducing agent, also described as a cross-oxidizing developing agent (COD), enables the sulfonamidodiphenylamine dye precursor to become oxidized without the sulfonamidodiphenylamine dye precursor itself developing silver. Alternatively, the cross-oxidizing reducing agent is viewed as an electron transfer agent which shuttles electrons between the developing silver halide and the sulfonamidodiphenylamine dye precursor.

The general requirements for a suitable cross-oxidizing reducing agent in a photographic silver halide material are: (a) the reducing agent must have sufficient electrochemical potential under the conditions of use to develop exposed silver halide; (b) in its oxidized form, the reducing agent must be of such electrochemical potential to oxidize the sulfonamidodiphenylamine dye precursor; and, (c) in its oxidized form, the reducing agent must be sufficiently stable to undergo the redox reaction with the sulfonamidodiphenylamine dye precursor. If any of the conditions are not met, the reducing agent is not a suitable cross-oxidizing developing agent for a silver halide photographic material. Whether a particular compound meets the requirements of a cross-oxidizing reducing agent depends upon the conditions under which the cross-oxidation reaction occurs. Other factors which influence the cross-oxidation reaction include the temperature of the process, the length of time required for cross-oxidation, and the pH of the composition in which cross-oxidation is to occur.

Examples of useful cross-oxidizing reducing agents include 3-pyrazolidone cross-oxidizing reducing agents. Preferred 3-pyrazolidone cross-oxidizing reducing agents include: 1-phenyl-3-pyrazolidone, 1-phenyl-4,4-dimethyl-3-pyrazolidone and 4-hydroxymethyl-4-methyl-1-phenyl-3-pyrazolidone. Such cross-oxidizing reducing agents are described in, for example, U.S. Pat. No. 3,938,995. Combinations of cross-oxidizing reducing agents are also useful, if desired. Combinations of non-cross-oxidizing silver halide developing agents and cross-oxidizing reducing agents are also useful if a minor proportion of the non-cross-oxidizing developing agent is present, such as less than about 10 percent of the total of the developing agents. Examples of combinations of a non-cross-oxidizing developing agent and a cross-oxidizing reducing agent include: 4-hydroxymethyl-4-methyl-1-phenyl-3-pyrazolidone with a minor proportion of at least one of the non-cross-oxidizing developing agents: ascorbic acid, hydroquinone and pyrimidine derivatives. Selection of an optimum silver halide developing agent or developing agent combination will depend upon such factors as the desired image, the particular photosensitive silver halide, processing conditions, and the particular phenazine dye to be formed.

The color-forming sulfonamidodiphenylamine dye precursors and the phenazine dyes according to the invention are useful in photographic materials comprising a photosensitive component which consists essentially of photographic silver halide. The photographic silver halide and the composition containing the photographic silver halide are prepared by any of the well known procedures in the photographic art, such as described in Research Disclosure, December 1978, Item No. 17643. The photographic composition is generally chemically sensitized and contains addenda such as brighteners, antifoggants, emulsion stabilizers, light absorbing or scattering materials, hardeners, coating aids, plasticizers, lubricants and antistatic materials, matting agents and development modifiers, which are also as described in Research Disclosure, December 1978, Item No. 17643.

The color-forming sulfonamidodiphenylamine dye precursor is generally immobilized in an oil phase in an imaging composition for use in an imaging material.

The photographic silver halide composition containing the color-forming sulfonamidodiphenylamine dye precursor or the phenazine dye is generally spectrally sensitized by means of spectral sensitizing dyes, as described in, for example, the above Research Disclosure Item No. 17643. Dyes which are useful for spectrally sensitizing silver halide photographic materials are selected from such classes of spectral sensitizing dyes as polymethine dyes, which include the cyanines, merocyanines, complex cyanines and merocyanines (including tri, tetra and polynuclear cyanines and merocyanines), as well as oxonols, hemioxonols, styryls, merostyryls and streptocyanines. Combinations of spectral sensitizing dyes are also useful.

The color-forming sulfonamidodiphenylamine dye precursor is useful in, for example, a photographic element comprising a support having thereon, in reactive association, in binder, such as a gelatino binder: (a) photosensitive silver halide, preferably in the form of a photosensitive gelatino silver halide emulsion, and (b) a color-forming sulfonamidodiphenylamine dye precursor according to the invention, wherein the element, upon imagewise exposure and processing by means of a cross-oxidizing photographic silver halide developer, produces a silver image and a phenazine dye image.

The described color-forming sulfonamidodiphenylamine dye precursor according to the invention is in any suitable location in the photographic material which produces the desired phenazine dye upon processing. The color-forming sulfonamidodiphenylamine dye precursor should be in a location with respect to the photosensitive silver halide which produces the desired dye image and the desired silver image upon processing. If desired, a proportion of the color-forming sulfonamidodiphenylamine dye precursor is in a layer contiguous to the layer of the photographic element comprising photosensitive silver halide. The term "in reactive association" as used herein means that the photosensitive silver halide and the color-forming sulfonamidodiphenylamine dye precursor are in a location with respect to each other which enables the photographic material upon processing to produce a desired phenazine dye image and a desired silver image.

In preparing an imaging composition comprising the color-forming sulfonamidodiphenylamine dye precursor, a dispersion solvent, also described herein as a coupler solvent, is useful to produce a coating composition. Many suitable coupler solvents known in the photographic art are also useful for aiding the dispersion of the sulfonamidodiphenylamine dye precursor or the corresponding phenazine dye produced upon processing. Examples of useful coupler solvents include N-n-butylacetnilide, diethyl lauramide, di-n-butyl phthalate and 2,4-ditertiaryamylphenol. The color-forming sulfonamidodiphenylamine dye precursor is also usefully loaded into a latex or a non-solvent dispersion is prepared, if desired.

Photographic elements according to the invention are usefully imagewise exposed by means of various forms of energy. The color-forming sulfonamidodiphenylamine dye precursor and the corresponding phenazine dye are relatively insensitive to light. However, the photosensitive component of the photographic element, such as photosensitive silver halide, is energy sensitive, especially photosensitive. The forms of energy which are useful to imagewise expose the photosensitive component include those to which photosensitive silver halide is sensitive and encompass such forms of energy as the ultraviolet, visible and infrared regions of the electromagnetic spectrum, as well as electron beam and beta radiation, gamma rays, X-rays, alpha particles, neutron radiation and other forms of corpuscular wave-like radiant energy, and either noncoherent (random phase) forms or coherent (in phase) forms, as produced by lasers. Imagewise exposure of the photographic material is monochromatic, orthochromatic or panchromatic, depending upon the spectral sensitization of the photosensitive silver halide. Imagewise exposure is generally for a sufficient time and intensity to produce a developable latent image in the photographic material.

The described photographic material containing the color-forming sulfonamidodiphenylamine dye precursor is processed either in a process which produces a positive phenazine dye image, or in a process which produces a negative phenazine dye image and silver image in the photographic material. The photosensitive silver halide contained in the photographic material is processed following exposure to form a visible image by associating the silver halide with an aqueous alkaline medium in the presence of a suitable developing agent contained in the medium or the photographic material.

If a reversal phenazine dye image is desired in the photographic material, a process is most useful in which a non-cross-oxidizing developing composition is used for processing the exposed photographic material as a first development step. During this step, the exposed silver halide is reduced to elemental silver by the non-cross-oxidizing developing composition. The non-cross-oxidizing developing composition does not, when oxidized, oxidize the color-forming sulfonamidodiphenylamine dye precursor to its corresponding phenazine dye.

The non-cross-oxidizing developer compositions useful in this step are generally alkaline solutions comprising a non-cross-oxidizing developing agent. Non-cross-oxidizing developing agents are well known in the photographic art and include many silver halide developing agents which will reduce exposed silver halide to silver, but will not oxidize the color-forming sulfonamidodiphenylamine dye precursor to a corresponding phenazine dye.

In a second step of the process for forming a reversal phenazine dye image, fogging is accomplished by exposing the photographic element to light or by chemical fogging by means of fogging compositions known in the photographic art.

Following the described fogging step, a second silver halide developing step is carried out. This is carried out by means of a cross-oxidizing developing composition. It is in this step that the phenazine dye image is formed. Many silver halide developing compositions are useful in this step, provided that the developing composition cross-oxidizes the color-forming sulfonamidodiphenylamine dye precursor to a desired phenazine dye. Such silver halide developing compositions include aqueous alkaline solutions comprising a cross-oxidizing silver halide developing agent, such as a 3-pyrazolidone cross-oxidizing silver halide developing agent. The cross-oxidizing developing agent becomes oxidized during development by reducing exposed or fogged silver halide to silver metal. The oxidized developer then cross-oxidizes the color-forming sulfonamidodiphenylamine dye precursor to produce a desired phenazine dye. A positive phenazine dye image is formed.

In preparing a phenazine dye from a color-forming sulfonamidodiphenylamine according to the invention for compositions and uses that are nonphotographic, other oxidizing agents are useful than the oxidized form of a cross-oxidizing developing agent. Such oxidizing agents include, for example, organic peroxides, such as benzoyl peroxide and hydrogen peroxide, inorganic peroxides, ferricyanides, dichromates and permanganates.

The following examples are included for a further understanding of the invention.

EXAMPLE 1

Preparation of 4-N,N-diethyl-2',4'-bismethanesulfonamidodiphenylamine

The following preparation was carried out:

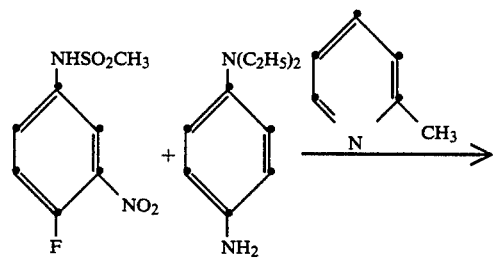

-continued

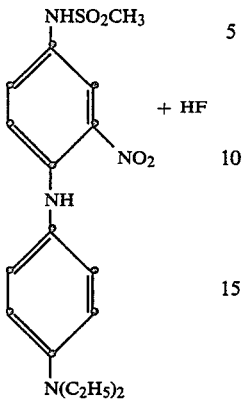

A solution of 42.1 g (0.18 mole) of the nitro compound and 29.5 g (0.18 mole) of the paraphenylenediamine compound in 250 ml of α-picoline (solvent) was refluxed overnight under nitrogen. The mixture was then poured over ice and, after the ice had melted, the mixture was filtered. The collected solid was washed with water until clear washings were obtained. Then the solid was air dried. The desired product was recrystallized from ethyl acetate to provide 53.6 g of red solid having a melting point of 168° C. to 170° C. The desired intermediate was also identified by elemental analysis.

Then the following reaction sequence was carried out:

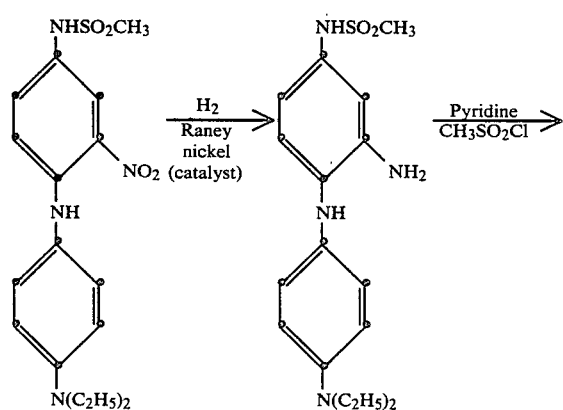

-continued

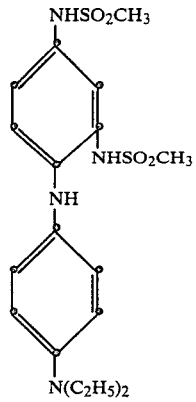

A solution of 20 g (0.053 mole) of the above nitro substituted compound in 400 ml of degassed tetrahydrofuran was reduced over Raney nickel catalyst at room temperature at 40 psi of hydrogen. The Raney nickel catalyst was removed by filtration, and the filtrate concentrated to dryness under nitrogen to protect the desired product from air oxidation. A dark blue gum was obtained. This was dissolved in 250 ml of pyridine and treated with methanesulfonyl chloride.

After stirring overnight at room temperature, the solution was poured into 2 liters of water and extracted twice with ethyl acetate. The extracts were combined, washed 5 times with water and dried over magnesium sulfate. After concentration to dryness, a deep red gum which had the odor of pyridine was obtained. This was dissolved in 75 ml of toluene and titrated with about 125 ml of ligroin. A product gummed out on the sides of the flask. After adding another 200 ml of ligroin, scratching the gum and vigorous stirring, solidification began. A dark rose colored solid was collected that had the odor of pyridine. The solid was dissolved in 100 ml of ethyl acetate, washed with water and dried over magnesium sulfate. Concentration to dryness yielded a bright red glass. Thin layer chromatography indicated one major air sensitive component, some magenta dye and several minor impurities. The product was recrystallized twice from 100 ml of toluene containing a trace of ethyl acetate to produce complete solution yielding a very pale pink solid having a melting point of 135° C. to 137° C. Mass spectrographic analysis and nuclear magnetic resonance analysis confirmed the identity of the desired product. The product was also identified by elemental analysis.

The phenazine dye form of the sulfonamidodiphenylamine product was identical to the phenazine dye generated oxidatively by means of $K_3Fe(CN)_6$. The maximum absorption (in butyl acetate) of the phenazine dye corresponding to the sulfonamidodiphenylamine was 472 nm.

EXAMPLES 2 THROUGH 6

The following sulfonamidodiphenylamines were also prepared according to the invention:

EXAMPLE 2

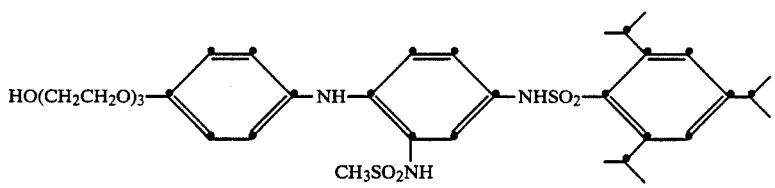

This compound had a melting point of 47° to 55° C.

EXAMPLE 3

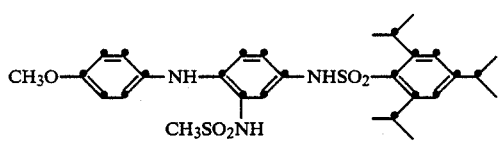

This compound had a melting point of 185° to 187° C.

EXAMPLE 4

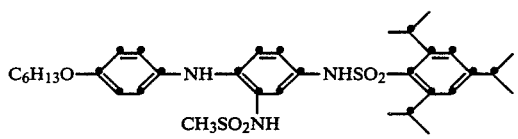

This compound had a melting point of 145° to 147° C.

EXAMPLE 5

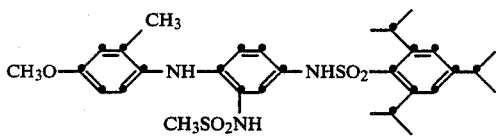

This compound had a melting point of 98° to 100° C.

EXAMPLE 6

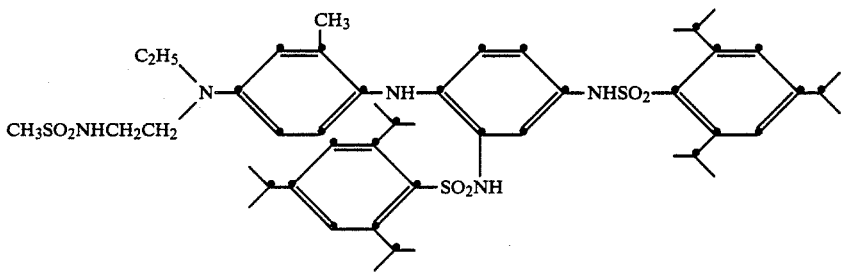

This compound had a melting point of 113° to 115° C.
The group represented by the structure:

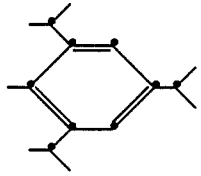

in each of Examples 2 through 6 means a 2,4,6-triisopropylphenyl group.

Each of the above compounds was also identified by elemental analysis.

EXAMPLES 7 AND 8

The corresponding phenazine dye was prepared for the sulfonamidodiphenylamine of Example 1 and for 4-methoxy-2',4'-bismethanesulfonamidodiphenylamine by means of the following procedure: A butyl acetate solution of the starting color-forming dye precursor was stirred rapidly with an aqueous solution of $K_3Fe(CN)_6$. After oxidation, the butyl acetate layer was washed with water and the solvent removed under reduced pressure to yield the desired phenazine dye. The following phenazine dyes were produced in this manner:

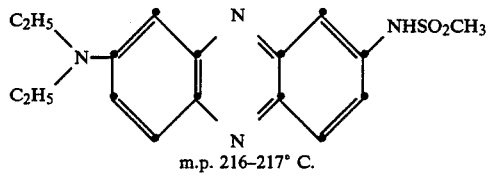

m.p. 216–217° C.

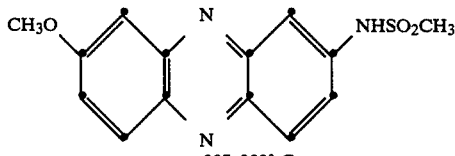

m.p. 287–289° C.

Each of the phenazine dyes was identified by elemental analysis.

EXAMPLE 9

Use in Photographic Element

A photographic silver halide element was prepared by coating the following layer on a poly(ethylene terephthalate) film support:

| | |
|---|---|
| silver bromide gelatino emulsion | 9.72 mg/dm² |
| gelatin (binder) | 43.2 mg/dm² |
| bis(vinylsulfonylmethyl)ether (gelatin hardener) | 0.432 mg/dm² |
| dye precursor: | 13.6 mg/dm² |

CH₃SO₂NHCH₂CH₂\
\\
N—⟨⟩—NH—⟨⟩—NHSO₂—⟨⟩\
/\
C₂H₅

(with CH₃ substituent, NHSO₂CH₃, and triisopropyl groups)

| | |
|---|---|
| di-n-butyl phthalate (coupler solvent) | 13.6 mg/dm² |

The resulting photosensitive silver halide layer was permitted to dry and was then overcoated by means of a gelatin composition containing gelatin (10.8 mg/dm²) and bis(vinylsulfonylmethyl)ether (hardener) (0.108 mg/dm²). A strip of the resulting photographic film was imagewise exposed through a step tablet in a commercial sensitometer to produce a developable image in the film. Processing was carried out at 22° C. by immersing the film in a tank containing a developer composition with agitation. The developer contained the following:

| | |
|---|---|
| Na₃PO₄.12H₂O | 47.5 g |
| 4-hydroxymethyl-4-methyl-1-phenyl-3-pyrazolidone | 1.0 g |
| benzyl alcohol | 10.0 ml |
| distilled water to | 1 liter |

The film was immersed in the described developer for 30 seconds and then rinsed with water for 60 seconds. The film was then fixed by immersing the developed film in a fixer composition containing the following components:

| | |
|---|---|
| Na₂S₂O₃.5H₂O | 248 g |
| Na₂CO₃.H₂O | 30 g |
| NaHCO₃ | 5 g |
| distilled water to | 1 liter |

The film was fixed for 30 seconds and then washed with water for 5 minutes. The film was then permitted to air dry.

The resulting developed silver plus dye image produced a maximum density in the first step of the step tablet of 1.2 and a minimum density in the eleventh developed step from the step tablet of 0.46. An orange phenazine dye image having a maximum absorption of 471 nm was generated during the described processing. This orange dye was a phenazine dye responding to the sulfonamidodiphenylamine dye precursor.

The phenazine dye image produced a maximum density of 0.79 to blue light.

The invention has been described in detail with particular reference to preferred embodiments thereof, but it will be understood that variations and modifications can be effected within the spirit and scope of the invention.

What is claimed is:

1. A phenazine dye represented by the formula:

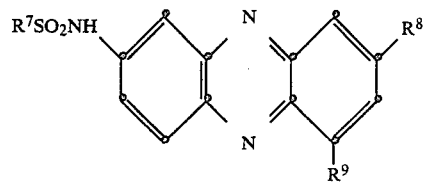

wherein:

$R^7$ is alkyl having 1 to 20 carbon atoms, phenyl, methoxyphenyl, triisopropylphenyl, tolyl, benzyl or xylyl;

$R^8$ is alkoxy having 1 to 20 carbon atoms, alkyl containing 1 to 20 carbon atoms, or

$R^9$ is hydrogen, alkyl having 1 to 4 carbon atoms or —NHSO₂R¹²;

$R^{10}$ is hydrogen or alkyl having 1 to 20 carbon atoms;

$R^{11}$ is alkyl having 1 to 20 carbon atoms; and, $R^{12}$ is alkyl having 1 to 20 carbon atoms, phenyl, methoxyphenyl, triisopropylphenyl, tolyl, benzyl or xylyl.

2. A phenazine dye as in claim 1 wherein $R^7$ is:

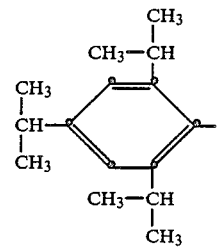

3. A phenazine dye which is 2-diethylamino-7-methanesulfonamido phenazine represented by the formula:

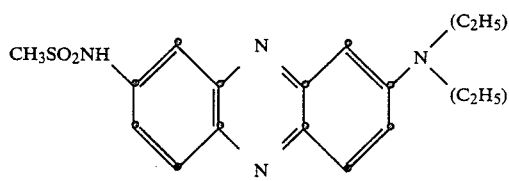

4. A phenazine dye which is 2-N-ethyl-N-(β-methanesulfonamido)ethylamino-4-methyl-7-(2,4,6-triisopropyl)phenylsulfonamido phenazine represented by the formula:

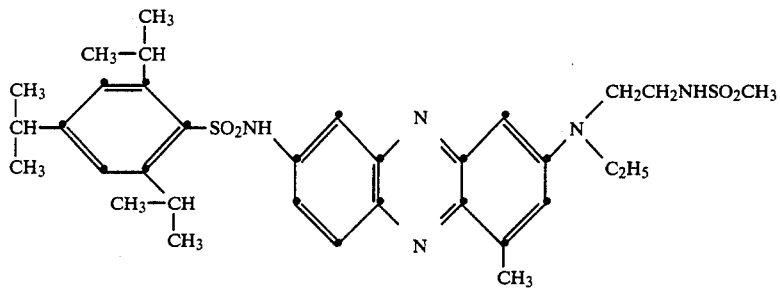
5. A phenazine dye which is 2-n-hexyloxy-7-(2,4,6-triisopropyl)phenylsulfonamido phenazine represented by the formula:
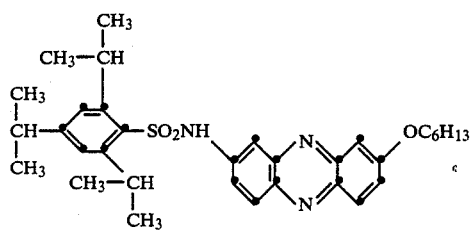
6. A phenazine dye which is 2-methoxy-7-(2,4,6-triisopropyl)phenylsulfonamido phenazine represented by the formula:
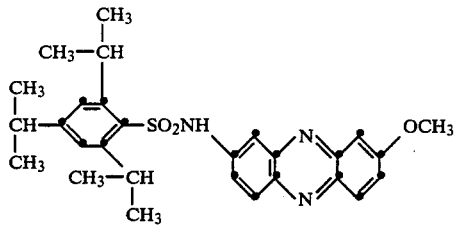
7. A phenazine dye which is 2-trisethoxyethanol-7-(2,4,6-triisopropyl)phenylsulfonamido phenazine represented by the formula:
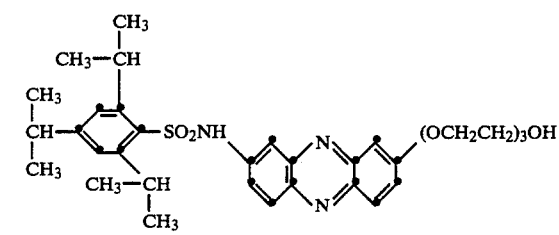
* * * * *